(12) United States Patent
Karapetyan

(10) Patent No.: US 6,991,460 B2
(45) Date of Patent: Jan. 31, 2006

(54) MULTIBRUSH TOOTH CLEANING APPARATUS WITH A SPRAY

(76) Inventor: Armen Karapetyan, 1935 N. Van Ness Ave., Los Angeles, CA (US) 90068

( * ) Notice: Subject to any disclaimer, the term of this patent is extended or adjusted under 35 U.S.C. 154(b) by 0 days.

(21) Appl. No.: 10/408,390

(22) Filed: Apr. 7, 2003

(65) Prior Publication Data
US 2004/0197733 A1  Oct. 7, 2004

(51) Int. Cl.
*A61C 17/02* (2006.01)
(52) U.S. Cl. ............................................. 433/98
(58) Field of Classification Search ................. 433/98, 433/80, 216; 601/162, 163, 165
See application file for complete search history.

(56) References Cited

U.S. PATENT DOCUMENTS

| | | | |
|---|---|---|---|
| 2,593,707 A * | 4/1952 | Thomas | 210/359 |
| 3,822,826 A * | 7/1974 | Wilson | 239/267 |
| 4,319,595 A * | 3/1982 | Ulrich | 132/309 |
| 5,142,723 A | 9/1992 | Lustig et al. | |
| 5,697,784 A | 12/1997 | Häfele et al. | |

\* cited by examiner

*Primary Examiner*—Melba N. Bumgarner

(57) ABSTRACT

A multibrush tooth cleaning apparatus with a spray provides a possibility to clean the teeth with the simultaneous flushing away the plaque debris and includes a fluid inlet tubular means coupled with the sink/bath faucet and with a main controllable valve installed on a stand. The stand comprises a fluid line, at least one of a plurality of fluid channels, an appropriate at least one of the same plurality of outlet pipes coupled with an appropriate at least one of the same plurality of the auxiliary controllable valves coupled by the flexible tubes with an appropriate at least one of the same plurality of the mouthpieces (tooth brushes). The outlet pipes are appropriately extended of the fluid line, and each of the outlet pipes is rigidly connected to the appropriate auxiliary controllable valve, comprising a lever intended to close or open the auxiliary controllable valve for fluid flow.

2 Claims, 4 Drawing Sheets

Fig. 4a
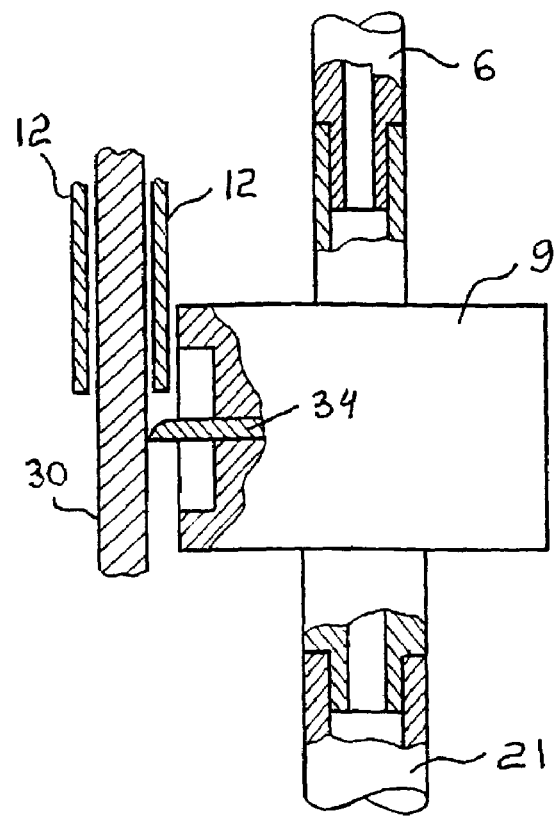
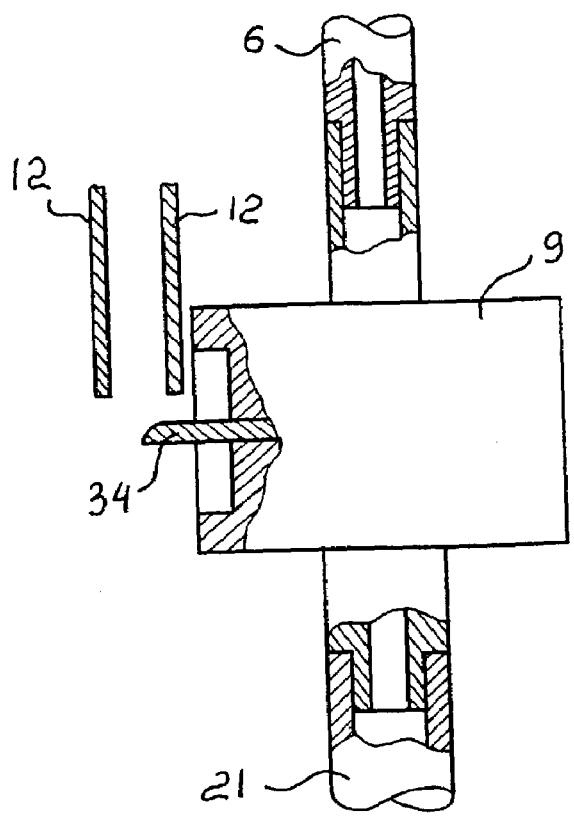
Fig. 4b

MULTIBRUSH TOOTH CLEANING APPARATUS WITH A SPRAY

FIELD OF THE INVENTION

This invention is generally related to dental hygiene devices and more particularly for tooth cleaning apparatus with a spray (fluid stream, jet) providing an appliance for multibrush tooth (multi-mouthpiece) cleaning with brushing action and with liquid spray or jet/stream action. The brush cleans a plaque from tooth surfaces and the jet flushes away the plaque debris.

BACKGROUND OF THE INVENTION

There is known, that dental hygiene devices, such as tooth brushes (mouthpieces) provide gingival stimulation and enhance the peripheral capillary dental circulation, and also conventional hand brushing dental hygiene practices are fairly efficient for cleaning smooth facial and lingual surfaces of the teeth because the bristle tips of a conventional toothbrush can readily access these broad surfaces. It is also known, that major incidences of tooth decay and of periodontal disease occur in interproximal areas such as crevices between adjacent teeth and the pits and fissures of the occlusal surfaces. Cleaning these areas with traditional hand brushing methods generally is unsatisfactory, with ineffective removal of residue and of dental plaque, and resulting in increased susceptibility to tooth decay and periodontal disease.

Some known techniques propose to solve these problems are powered brushes, in which the entire brush head is moved while water or another fluid is emitted from the brush head. Other prior art techniques are powered brushes in which the brush head has rotating tufts and/or longitudinal (reciprocating) movements of bristles, and liquid jet devices. For example, U.S. Pat. No. 5,142,723 describes a tooth cleaning apparatus having powered brush and spray and includes a housing that provides a manually deployable handle for the device and that houses a motor that drives both a brush agitating drive mechanism, and a liquid dispensing pump mechanism. The housing has a tool mount that interchangably mounts in operable relation with the drive mechanism and with the pump mechanism any one of a dental brush tool and a dental spray tool. The brush tool and the drive mechanism preferably are arranged to agitatingly drive two sets of brush elements and oppositely, preferably with back and forth rotation of individual brush tufts.

The motor is powered either by batteries mounted within the housing or from an external power source, has an output shaft a centered on the axis and mechanically coupled to rotate a beveled gear about the axis. The beveled gear is drivingly engaged with a pair of cranking bevel gears and. The cranking gears and are rotatable about a common axis, perpendicular to the axis, by way of shaft screws that mount each gear to a support frame that in turn is seated within the housing. The cranking gears 46 and 48 are spaced apart along the axis. A crank rod is pinned to the periphery of the cranking gear 46 and a similar crank rod is pinned to the cranking gear. Each crank rod and extends generally along the direction of axis and is rotatably fastened at its end remote from its respective cranking gear to one reciprocating rod and, respectively. The reciprocating rods extend side-by-side along the direction of axis and are axially slidable relative to the housing.

Such device is very complex, requires a liquid dispensing pump mechanism, and does not provide the possibility for multibrush use.

In some other known dental cleaning devices, the dental-jet device whose grip member comprises a control means in the form of an adjustment wheel. The adjustment wheel is connected to a rotatable valve body of a valve provided as fluid-flow control means. An amount of fluid which flows through the fluid channel in a given time interval, which fluid is supplied to the mouthpiece of the dental-jet device and is adequate for a normal cleaning operation, is adjustable by turning the valve body by means of the adjustment wheel in order to supply this amount of fluid. The amount of fluid is below a maximum possible flow and is selected by the user, is supplied to the mouthpiece of the dental-jet device. In order to increase the fluid supply to the mouthpiece after the fluid flow has been adjusted by means of the adjustment wheel, for example in order to remove very persistent residual food particles, the adjustment wheel on the grip member of the known dental-jet device should be rotated from a previously selected setting for a desired fluid flow to a setting for an increased fluid flow. As a result the previously selected setting of the adjustment wheel for the previously desired fluid flow adequate for a normal cleaning operation is lost. Moreover, in the known dental-jet device the fluid flow supplied to a mouthpiece cannot be increased beyond the maximum fluid flow dictated by the dimensioning of the fluid channel and the fluid-flow control means. For example, in U.S. Pat. No. 5,697,784 a dental cleaning device is provided with a mouthpiece and with a grip member having a fluid channel and having a fluid-flow control device located on the brush body, which is adjustable an actuating member, which is movable between different actuating positions to change the amount of fluid supplied to the mouthpiece through the fluid channel, the grip member is provided with activatable parts for temporarily increasing the amount of fluid supplied to the mouthpiece while the instantaneous actuating position of the actuating member for the fluid-flow control device.

The grip member comprises a slide knob which is guided so as to be movable in the longitudinal direction of the grip member indicated by the arrow and in a direction opposite thereto, between an "off"-position and an "on"-position. When the slide knob 11 is in the "on"-position the water supply from the tube to the mouthpiece via the grip member is interrupted and when the slide knob is in its "on"-position water supply from the tube to the mouthpiece via the grip member is possible. A push-button included in the slide knob has a part which points away from the grip member and traverses the slide knob. The grip member of the dental-jet device has an elongate sleeve-shaped plastic housing comprising a first housing section, situated nearest a mouthpiece, and a second housing section, whose end adjoins the end of the first housing section at the location of the flexible adjustment ring. At its free end the first housing section has an opening through which the interior of an inner tubular housing portion is accessible. A mouthpiece is inserted into the tubular housing portion through the opening to couple this mouthpiece to the grip member in a fluid-transmitting manner. At its free end the second housing section has a bottom. The tubular portion of the first housing section is adjoined by a plastic tubular coupling member located in the first housing section and having a comparatively thick-walled portion into which the end of a mouthpiece can be introduced. At the location of the comparatively thick-walled portion a wire spring is arranged having a circular shape over an angle of substantially 270 degree and having straight end portions which extend substantially parallel to one another and towards the interior of the circular spring. The two spring ends hold a mouthpiece onto the grip member in that the spring ends engage a groove in the mouthpiece 6. The end of a mouthpiece held by means of the spring then lies against a sealing ring fitted in the comparatively thick-walled portion of the coupling member.

This device is complex too and expensive, and is intended for one tooth brush only.

Thus, there is a great need in the art for the improved family oriented multibrush tooth cleaning apparatus with a spray (fluid stream, jet), providing convenient, economical and effective cleaning of the teeth with the flushing away the plaque debris.

OBJECT AND ADVANTAGES OF THE INVENTION

Accordingly, several objects and advantages of the present invention are to provide convenient, economical and effective tooth cleaning.

It is further object of the invention to increase efficiency of the dental hygiene.

It is still further object of the invention to increase convenience of the family dental hygiene.

It is another object of the invention to eliminate necessity of the manual moisturizing of the tooth brush during tooth cleaning process.

It is still another object of the invention to provide convenient control of the fluid spray/stream flow.

Still, further objects and advantages will become apparent from a consideration of the ensuing description accompanying drawings.

DESCRIPTION OF THE DRAWING

In order that the invention and the manner in which it is to be performed may be more clearly understood, embodiments thereof will be described by way of example with reference to the attached drawings, of which:

FIGS. 4a, 4b are a simplified drawing of the auxiliary controllable valve's button operation.

SUMMARY OF THE INVENTION

In view of the foregoing disadvantages inherent in the known prior art, the present invention provides a new multibrush tooth cleaning apparatus with a spray/stream eliminating the manual moisturizing of the tooth brush during tooth cleaning process. As such, the general purpose of the present invention, which will be described hereinafter in greater details, is to provide a new multibrush tooth cleaning apparatus with a spray/stream, which has many of the advantages of the family dental hygiene devices with a spray (et stream) mentioned heretofore and many novel features that result in the multibrush tooth cleaning apparatus, which is not anticipated, rendered obvious, suggested or even implied by any of prior art dental hygiene devices, either alone or in any combination thereof.

To attain this, the present invention generally comprises a fluid inlet tubular means coupled with the sink/bath faucet and with a main controllable valve installed on a stand including a fluid line, at least one of a plurality of fluid channels, an appropriate at least one of the same plurality of outlet pipes coupled with an appropriate at least one of the same plurality of the auxiliary controllable valves appropriately coupled by the flexible tubes with an appropriate at least one of the same plurality of the mouthpieces (tooth brushes). The outlet pipes are appropriately extended of the fluid line, and each of the outlet pipes is rigidly connected to the appropriate auxiliary controllable valve, comprising a lever, intended to close or open the auxiliary controllable valve for fluid flow.

DESCRIPTION OF THE PREFERRED EMBODIMENTS

Here the description of an improved multibrush tooth cleaning apparatus with a spray will be done in statics (as if the components of the improved apparatus are suspended in the space) with description of their relative connections to each other. The description of the functional operations of an improved apparatus will be done hereinafter.

Figure 1:
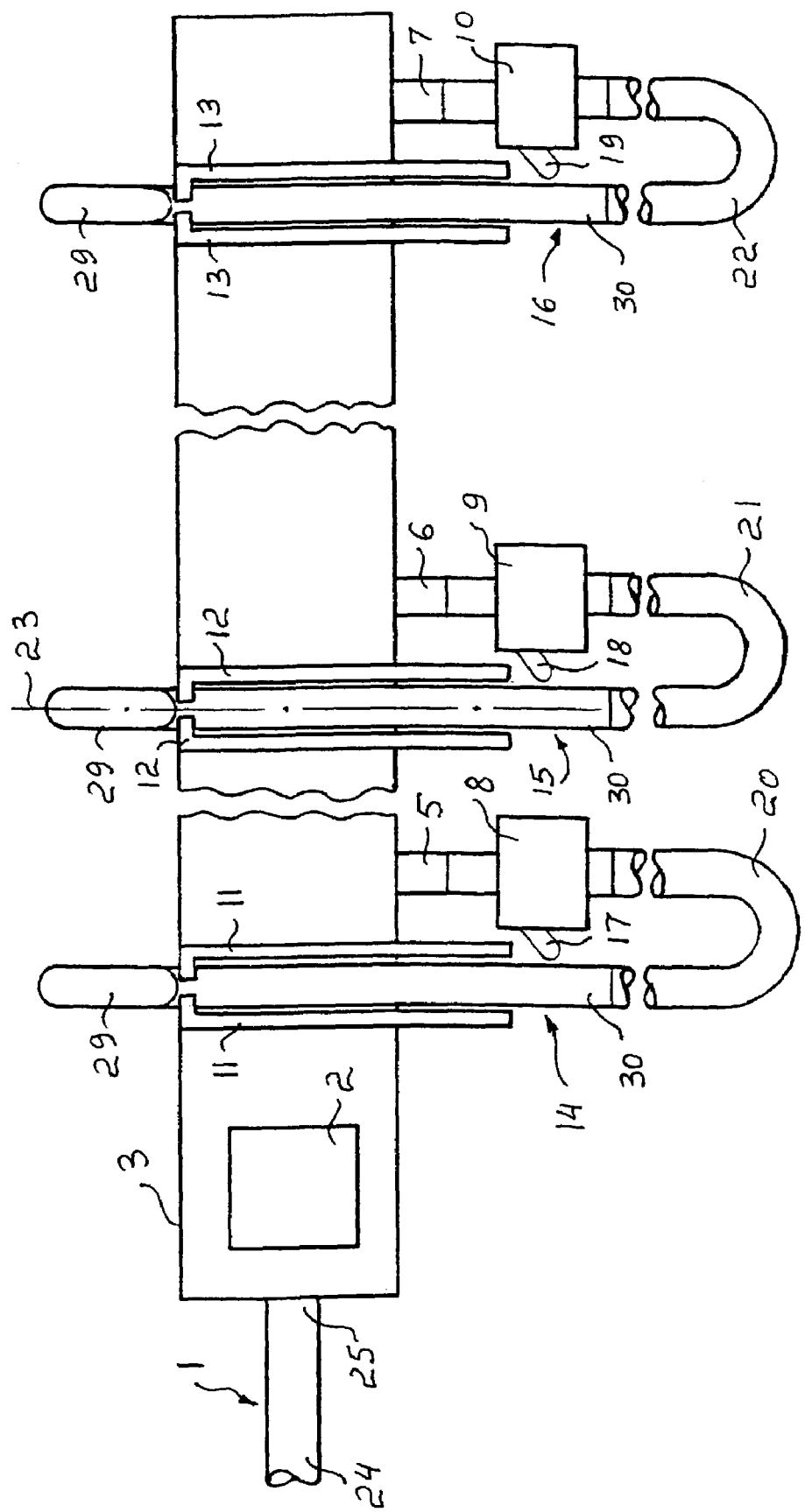
FIG. 1 is a simplified drawing of an improved multibrush tooth cleaning apparatus with a spray.
Figure 2:
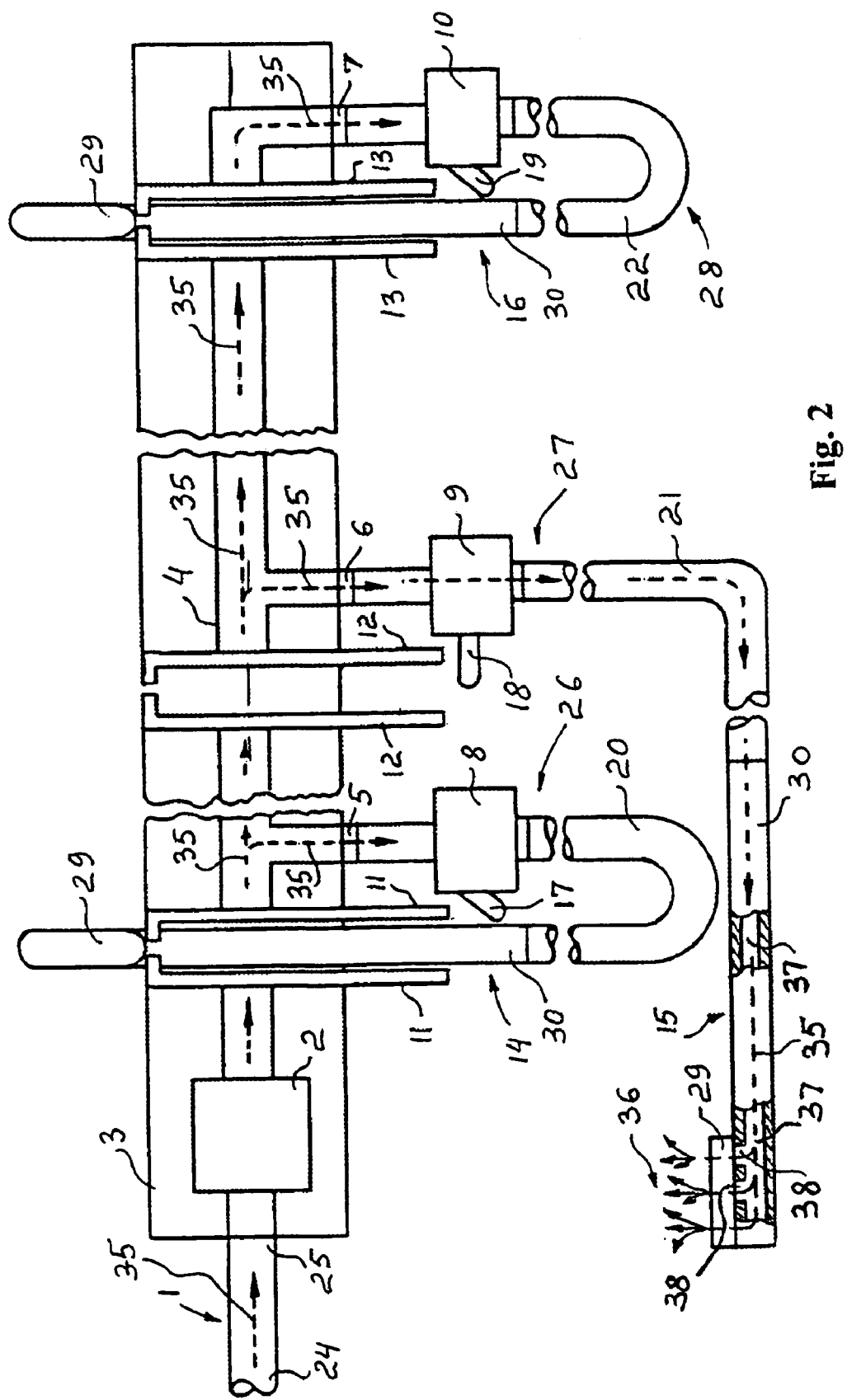
FIG. 2 is a simplified illustration of the fluid flow.
Figure 3A:
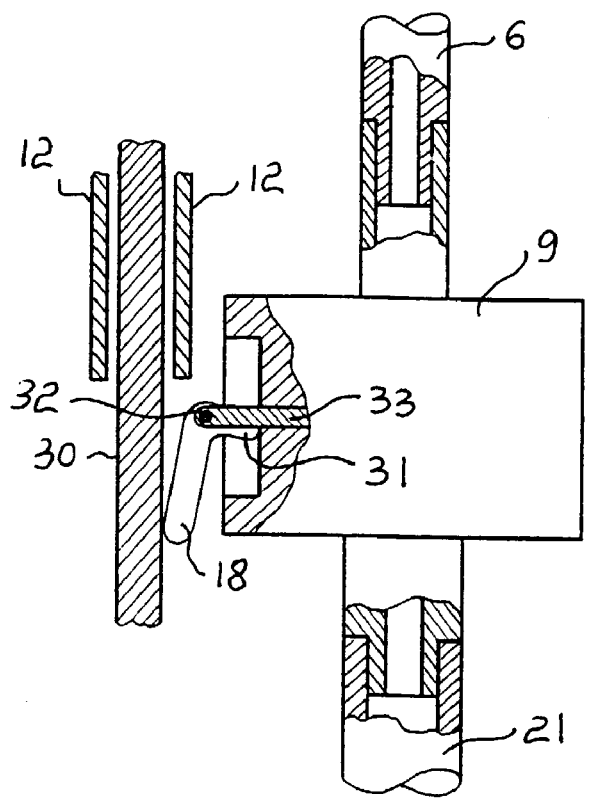
FIGS. 3a, 3b are a simplified drawing of the auxiliary controllable valve's lever operation.
Figure 3B:
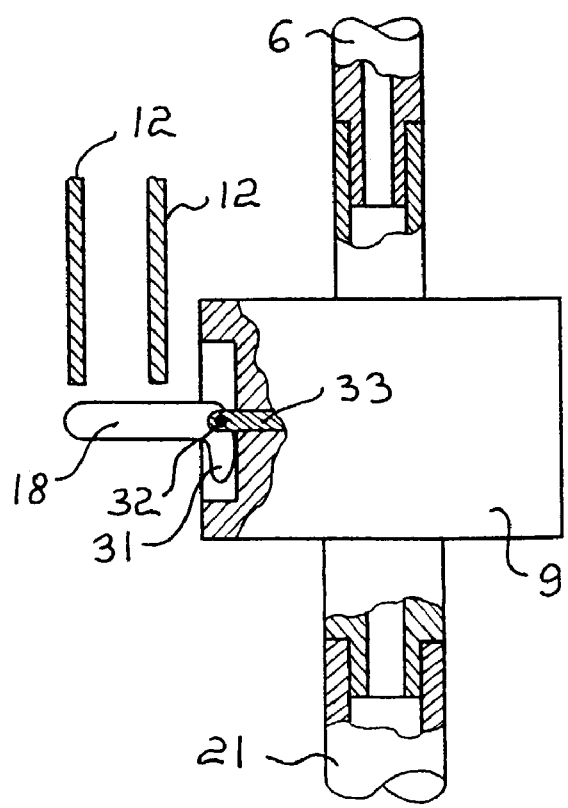

An improved multibrush tooth cleaning apparatus with a spray includes a fluid (preferably water) inlet tubular means 1 coupled by an inlet side 24 with the sink/bath faucet (not shown), and by its outlet side 25 with a main controllable valve 2 installed on a stand 3. The stand 3 comprises a fluid line 4, at least one of a plurality "N" (N=1, 2, . . . , i, . . . , n–1, n) of fluid channels (on FIGS. 1, 2 are conventionally shown three fluid channels, i.e: the first fluid channel 26, the i-th fluid channel 27 and the n-th fluid channel 28) and appropriately at least one of the same plurality "N" of outlet pipes (on FIG. 1 are conventionally shown three outlet pipes, i.e: the first outlet pipe 5, the i-th outlet pipe 6 and the n-th outlet pipe 7), appropriately at least one of a plurality "N" of the auxiliary controllable valves (on FIG. 1 are conventionally shown three auxiliary controllable valves, i.e: the first auxiliary controllable valve 8, the i-th auxiliary controllable valve 9 and the n-th auxiliary controllable valve 10), appropriately at least one of a plurality "N" of the holders (on FIG. 1 are conventionally shown three holders, i.e: the first holder 11, the i-th holder 12 and the n-th holder 13), appropriately at least one of a plurality "N" of the tooth brushes (on FIG. 1 are conventionally shown three tooth brushes, i.e: the first tooth brush 14, the i-th tooth brush 15 and the n-th tooth brush 16). The outlet pipes 5–7 are appropriately extended of the fluid line 4. Each auxiliary controllable valve is rigidly connected to the appropriate outlet pipe and comprises a lever (on FIG. 1 are conventionally shown three levers, i.e: the first lever 17 of the first auxiliary controllable valve 8, the i-th lever 18 of the i-th auxiliary controllable valve 9, and the n-th lever 19 of the n-th auxiliary controllable valve 10 respectively). Each lever is coupled with an appropriate auxiliary controllable valve and intended to close or open the auxiliary controllable valve for fluid flow. The controlling element of the auxiliary valve, such as a lever, is not limited by lever only, for example, the auxiliary controllable valve can have a button/knob 34, shown on FIGS. 4a, 4b, instead of the lever. The button 34 is spring-actuated (spring is not shown) and provides the same "open-close" functions for auxiliary controllable valve. When the mouthpiece, for example i-th mouthpiece 15 is inserted into holders 12, the button 34 is in the "pushed-in" position adequate to closed auxiliary controllable valve 9 (see FIG 4a), and when mouthpiece is in use, the button 34 is extended (see FIG. 4b), and the auxiliary controllable valve 9 is open for fluid flow. Each lever is spring-actuated by the spring (not shown), keeping the lever initially in the horizontal position (for button—in the extended horizontal position). The spring (not shown) can be of plane or spiral configuration. Each outlet pipe is respectively connected to an appropriate tubular means (on FIG. 1 are conventionally shown three tubular means, i.e: the first tubular means 20, the i-th tubular means 21 and the n-th tubular means 22). The simplified connection of the outlet pipe and tubular means is shown on FIGS. 3a–4b with regard, for instance, to the i-th fluid channel. Each tooth brush includes the fluid passage 37 (see FIG. 2) located inside mouthpiece (tooth brush) along longitudinal axis 23, and apertures 38 (see FIG. 2) located in the bristle area of the bristle portion 29 and connected to the fluid passage 37. The bottom of the handle portion 30 of each tooth brush is connected to an appropriate tubular means.

The improved multibrush tooth cleaning apparatus with a spray operates as follows below. In the initial state (for example, all tooth brushes are inserted in the appropriate holders and the main controllable valve 2 is closed). At this state, all levers of all auxiliary valves are "down" in the vertical positions (see FIG. 3a) which correspond to their closed position. In this position the eccentric 31 of the lever 18 extends rod 33 of the auxiliary controllable valve 9, thereby closing valve 9 for fluid flow (the eccentric 31 is coupled with the rod 33 by the pin 32, as shown on FIGS. 3a, 3b). At the time when the user pulls his/her personal tooth brush (for instance, the i-th tooth brush 15) from the appropriate i-th holder 12, the i-th lever's spring (not shown) actuates the i-th lever 18 moving it in the its horizontal position (FIG. 3b), thereby opening the auxiliary controllable valve 9 for fluid flow. Then the user open the faucet's valve (not shown), and when the user is ready to spray/jet the fluid to the teeth, he/she open the main controllable valve providing the fluid flow 35 into fluid line 4, as shown on FIG. 2. The fluid flows from the opened main controllable valve 2 along the fluid line 4, through the i-th outlet pipe 6, opened i-th auxiliary controllable valve 9, i-th tubular means 21, fluid passage 37 into handle portion 30 of the i-th tooth brush 15 to the apertures 38 located into bristle area of the bristle portion 29, and through the apertures of the bristle portion 29 of the i-th tooth brush 15 to the teeth, thereby spraying (sprinkling) the teeth by fluid, providing both: the brush cleans a plaque from tooth surfaces and the jet/stream 36 flushes away the plaque debris. The fluid pressure (flow) can be controlled either by sink/bath faucet's valve (not shown) or by the main controllable valve 2, that is more convenient. When the dental hygiene procedure is completed, the user turns-off (closes) the main controllable valve 2, closing the fluid line for the fluid flow, and installs the i-th tooth brush 15 in the i-th holder 12, thereby closing the i-th auxiliary controllable valve 9.

The stand 3 can be attached, for example to the wall near the bathroom sink. The tubular means are preferably flexible and can have crimped (goffered) configuration. The stand, outlet pipes and holders can be made of any kind of material (preferably of plastic). The holder can preferably be slightly flexible in order to slightly clamp the mouthpiece (tooth brush). The auxiliary controllable valve may not include any levers or buttons, providing automatic opening or closing of the auxiliary controllable valve by installing or pulling out the tooth brush from the holder, and provide the opening or closing of the auxiliary controllable valve manually by handle installed on the auxiliary controllable valve. Also the auxiliary valves (such as auxiliary valves 8–10 on FIGS. 1, 2) can be installed in the mouthpiece, and opening/closing of the fluid flow can be provided by controlling lever or button installed on the mouthpiece opening or closing the fluid flow through mouthpiece. The tubular means (such as 20–22 on FIGS. 1, 2) preferably have smaller diameter than cross-section of the handle portion of the mouthpiece.

Thus, an improved multibrush tooth cleaning apparatus with a spray provides family convenient, economical and effective dental hygiene.

CONCLUSION, RAMIFICATION AND SCOPE

Accordingly the reader will see that, according to the invention, I have provided a multibrush tooth cleaning apparatus with a spray, providing convenient, economical and effective dental hygiene for family. An improved multibrush tooth cleaning apparatus with a spray has various possibilities, considering activities of the tooth cleaning devices.

While the above description contains many specificities, these should be not construed as limitations on the scope of the invention, but as exemplification of the presently-preferred embodiments thereof. Many other ramifications are possible within the teaching to the invention. For example, an improved apparatus including a multibrush wall stand eliminates the necessity to use the movable unstable tooth brush stands for the bathroom sink. An improved multibrush tooth cleaning apparatus is universal and convenient for entire family, providing elimination of the accidental misplace of the personal tooth brush. Also, such apparatus eliminates the necessity of the manual moisturizing of the tooth brush during dental hygiene procedure.

Thus, the scope of the invention should be determined by the appended claims and their legal equivalents, and not by examples given.

THE DRAWING REFERENCE NUMERALS WORKSHEET

1.—an inlet tubular means;
2.—a main controllable valve;
3.—a stand;
4.—a fluid line;
5.—a first outlet pipe;
6.—an i-th outlet pipe;
7.—a n-th outlet pipe;
8.—a first auxiliary controllable valve;
9.—an i-th auxiliary controllable valve;
10.—a n-th auxiliary controllable valve;
11.—a first holder;
12.—an i-th holder;
13.—a n-th holder;
14.—a first mouthpiece (tooth brush);
15.—an i-th mouthpiece (tooth brush);
16.—a n-th mouthpiece (tooth brush);
17.—a first lever;
18.—an i-th lever;
19.—a n-th lever,
20.—a first tubular means;
21.—an i-th tubular means,
22.—a n-th tubular means,
23.—a longitudinal axis;
24.—an inlet side of the inlet tubular means 1;
25.—an outlet side of the inlet tubular means 1;
26.—a first fluid channel;
27.—an i-th fluid channel;
28.—a n-th fluid channel;
29.—a bristle portion of the mouthpiece;
30.—a handle portion of the mouthpiece;
31.—an eccentric;

32.—a pin;
33.—a rod;
34.—a button;
35.—a fluid flow;
36.—a fluid spray (jet/stream).

What is claimed is:

1. A multibrush tooth cleaning apparatus with a spray comprising
a stand of said multibrush tooth cleaning apparatus with said spray, wherein said stand includes a fluid line and at least two of a plurality of fluid channels extended from said fluid line, and a main controllable valve installed on said stand between said fluid line and an inlet tubular means coupled with a faucet of a sink; wherein each of said fluid channels comprises
an outlet pipe by one end extended from said fluid line of said stand and by another end is coupled with an auxiliary controlable valve including a lever providing opening or closing of said auxiliary controllable valve for a fluid flow;
a tubular means coupled by a first end with said auxiliary controllable valve;
a mouthpiece coupled by said tubular means with said auxiliary controllable valve, and wherein said mouthpiece comprises
a handle portion coupled with a second end of said tubular means, wherein said handle portion includes a fluid passage providing the flow of the fluid, and wherein said fluid passage is located inside said mouthpiece along longitudinal axis of said mouthpiece;
a bristle portion coupled with said handle portion and including apertures providing said spray of said fluid flow flowing to said apertures by said fluid passage;
a holder intended for clamping of said handle portion of said mouthpiece and attached to said stand, wherein said holder is located in an area adjacent to said lever of said auxiliary controllable valve, and wherein the insertion of said handle portion of said mouthpiece into said holder provides closing of said fluid flow through said auxiliary controllable valve.

2. The apparatus of claim 1, wherein each of said auxiliary controllable valves further includes a button, providing said opening/closing of said auxiliary controllable valve for said fluid flow.

* * * * *